(12) United States Patent
George et al.

(10) Patent No.: US 9,597,810 B2
(45) Date of Patent: Mar. 21, 2017

(54) SCISSORS

(76) Inventors: Samuel George, Weybridge (GB); Hani Musleh, Weybridge (GB)

(*) Notice: Subject to any disclaimer, the term of this patent is extended or adjusted under 35 U.S.C. 154(b) by 113 days.

(21) Appl. No.: 13/984,619

(22) PCT Filed: Feb. 10, 2012

(86) PCT No.: PCT/GB2012/050297
§ 371 (c)(1),
(2), (4) Date: Oct. 15, 2013

(87) PCT Pub. No.: WO2012/107775
PCT Pub. Date: Aug. 16, 2012

(65) Prior Publication Data
US 2014/0026426 A1    Jan. 30, 2014

(30) Foreign Application Priority Data

Feb. 10, 2011 (GB) .................................. 1102308.2
Aug. 12, 2011 (GB) .................................. 1113917.7

(51) Int. Cl.
*B26B 13/28* (2006.01)
*B26B 13/12* (2006.01)

(52) U.S. Cl.
CPC ............ *B26B 13/285* (2013.01); *B26B 13/12* (2013.01)

(58) Field of Classification Search
CPC ....... B26B 13/00; B26B 13/005; B26B 13/04; B26B 13/12; B26B 13/26; B26B 13/28; B26B 13/285
USPC ........................................ 30/232–262; D8/57
See application file for complete search history.

(56) References Cited

U.S. PATENT DOCUMENTS

| | | | | |
|---|---|---|---|---|
| 861,713 A | * | 7/1907 | Dow ..................... | B26B 13/285 30/268 |
| 1,618,082 A | * | 2/1927 | Hafner ................. | B26B 13/285 30/268 |
| 2,009,502 A | * | 7/1935 | Lambert ................ | B26B 13/04 30/260 |
| 3,971,131 A | * | 7/1976 | Boyajian .............. | B23D 29/026 30/260 |
| 3,972,333 A | * | 8/1976 | Leveen ........................ | 606/174 |

(Continued)

FOREIGN PATENT DOCUMENTS

| DE | 3721261 A1 | 2/1988 |
|---|---|---|
| GB | 2423269 | 8/2006 |
| JP | 2002045582 | 2/2002 |

*Primary Examiner* — Jason Daniel Prone
*Assistant Examiner* — Richard Crosby, Jr.
(74) *Attorney, Agent, or Firm* — Baker & Hostetler LLP (57) ABSTRACT

Scissors, especially surgical scissors, having first and second elongate members each having a handle portion and a blade portion and being connected by a pivot between the handle portions and the blade portions for relative pivotal movement generally in a cutting plane during a cutting stroke. At least one of the handle portions supports a channel member having a length that extends toward, embraces and extends beyond the handle portion of the other elongate member to restrain movement of the handle portions out of the cutting plane and thus to resist relative lateral movement of the blade portions away from each other during the cutting stroke. The scissors are robust and are able to cleanly, effectively and accurately cut tough or slippery items which might otherwise cause the blades to splay away from each other.

17 Claims, 5 Drawing Sheets

(56) References Cited

U.S. PATENT DOCUMENTS

| | | | | |
|---|---|---|---|---|
| 4,776,096 A | * | 10/1988 | Chang | 30/233 |
| 5,093,996 A | * | 3/1992 | Gross | 30/245 |
| 6,883,239 B2 | * | 4/2005 | Sato | 30/236 |
| 6,915,578 B2 | * | 7/2005 | Yusufov | B26B 13/00 |
| | | | | 30/232 |
| 8,832,945 B2 | * | 9/2014 | Yang | B26B 13/16 |
| | | | | 30/254 |
| 2009/0271987 A1 | * | 11/2009 | Fisher | 30/123 |
| 2015/0047209 A1 | * | 2/2015 | Schmidt | 30/233 |

\* cited by examiner

SCISSORS

FIELD

The present invention relates to scissors and more particularly but not exclusively to surgical scissors.

BACKGROUND

Surgical scissors are indispensable tools for surgeons, operating theatre staff and other medical practitioners and are used for cutting and excising patient tissue or sutures. These scissors need to be able to cut cleanly, effectively and accurately, to be robust, and to be suitable for sterilisation. It can be appreciated that accuracy of cutting is important in any surgical procedure. Achieving a clean cut is particularly important for minimising trauma and inflammation to the surrounding tissue.

Conventional surgical scissors comprise two scissor members, each scissor member having a distal blade portion and a proximal handle portion. The blade portion has a cutting edge, a contacting face, an outer face and a distal tip. A finger opening is at the proximal end of the handle portion. The scissor members are pivotally connected to each other at a pivot axis between the blade portion and the handle portion such that their contacting faces can mutually abut when closed. As with conventional scissors, as the distal tips of the blade portions are moved closer together by squeezing together the handle portions, the contacting faces of the blade portions slide relative to each other parallel to their planes. In so doing, the respective cutting edges mutually intersect and contact each other at a point of contact which travels distally along the cutting edges as the blade members come together. Cutting is achieved by the shearing action of the opposed cutting edges of the blade portions at the point of contact. Conventionally, surgical scissors are ergonomically adapted for either left-handed or right-handed use.

This conventional scissor design is ineffective when cutting tough fibrous tissue such as ligaments, or large sections of tissue. In those situations, the blade members of the scissors tend to splay apart or the tissue slips away, thus achieving either an imprecise cut or no cut at all. In addition, the misalignment caused by the blade members splaying apart can result in tissue becoming trapped between the splayed blade members rendering the scissors useless until the trapped tissue is freed. In order to minimise the chances of blade splaying, the surgeon must perform a number of smaller cuts on tough tissue as opposed to one clean cut. However, a series of small cuts, results in an imprecise, untidy and ragged cut; it also prolongs the procedure.

Often, surgical scissors are unable to withstand the rigours of surgery and sterilisation. They may need to be repaired frequently or discarded and replaced. Commonly, the two blades are held against each other by a pivot pin which loosens and increases the risk of the blades splaying apart in use. Also the blades tend to become blunt on recurrent use and hence require frequent sharpening.

A possible way of overcoming some disadvantages of conventional surgical scissors would be to use stiffer blades so that they do not splay apart as readily. Stiffer blades may be achieved by using a stiffer material, which would be more expensive, or by making the blades thicker. However, thicker blades are both undesirable and impractical as the scissors may be too bulky to manoeuvre in confined spaces, heavier and therefore more tiring to use, and more expensive to make. Furthermore, surgeons are familiar with their conventional instruments, particularly with the weight and feel of their instruments in use, therefore it is desirable for any adaptations to conventional surgical scissors to be minimal so that surgeons remain comfortable with using the scissors. In addition, it is desirable for any adaptations to be minimal so as to keep the cost of manufacture low.

JP 2002045582 discloses scissors comprising removable handles. The removable handles are connected together by a guide part so that the handles do not become disassociated from one another when the handles are detached from the blades.

This document does not address the problem of lateral blade splaying in scissors during cutting.

The inventor has previously come up with a solution to the problem of lateral blade splaying. GB 2,423,269 discloses scissors comprising a wedge means on at least one of the handle portions, the wedge means being co-operable with the other handle portion during a cutting stroke to urge the handle portions apart laterally while biasing the blade portions laterally together to oppose relative lateral movement of the blade portions away from each other during the cutting stroke.

There remains a desire for surgical scissors that address the problem of lateral blade splaying, whilst remaining closely related to conventional surgical scissors so as to keep the cost of manufacture low and to increase acceptance in the market.

An object of the present invention is to provide improved scissors that are robust, cut cleanly and effectively and avoid or minimise the disadvantages of current scissors as outlined above.

SUMMARY

In a first aspect, the present invention resides in scissors having first and second elongate members each having a handle portion and a blade portion and being connected by a pivot between the handle portions and the blade portions for relative pivotal movement generally in a cutting plane during a cutting stroke, wherein at least one of the handle portions supports a channel member having a length that extends toward, embraces and extends beyond the handle portion of the other elongate member to restrain movement of the handle portions out of the cutting plane and thus to resist relative lateral movement of the blade portions away from each other during the cutting stroke.

The channel member may comprise arms that extend from the handle portion supporting the channel member toward the handle portion of the other elongate member so as to embrace the handle portion of the other elongate member between them.

The arms may extend parallel to one another and a base may join the arms together. Suitably, the channel member may be U-shaped in transverse cross-section.

Alternatively, the arms may be joined together at both ends of the channel member such that the channel member is a closed loop. Suitably, the channel member may be substantially rectangular in transverse cross-section. A closed loop configuration is advantageous because it avoids any divergence or lateral splaying of the arms of the channel member.

It is also possible for the channel member to embrace the handle portion on which it is supported.

Suitably, the channel member may be located approximately midway along the length of the handle portion on which it is supported. Such positioning decreases the risk of the user's thumb and/or finger interfering with the channel member whilst providing for effective restraint of relative lateral splaying movement of the blade portions away from one another during the cutting stroke.

The channel member may be integral with the handle portion on which it is supported or alternatively it may be formed separately from and be attached to the handle portion on which it is supported. Preferably, the channel member may be attached to the handle portion on which it is supported by welding.

The arms may lie parallel to the cutting plane, suitably with one arm each side of the cutting plane.

Each of the arms may comprise an inner face and an inner side of at least one of the arms may bear against the handle portion of the other elongate member. Suitably, the handle portion of an elongate member may be slidably movable within and along the length of the channel member in the cutting plane.

The longitudinal thickness of the channel member may occupy a minority of the length of the handle portions.

The channel member may extend in a direction substantially perpendicular to the length of the handle portion on which it is supported or alternatively the channel member may be inclined distally with respect to the length of the handle portion on which it is supported. Furthermore, the channel member may curve distally along its length from the handle portion on which it is supported.

BRIEF DESCRIPTION OF THE DRAWINGS

In order that this invention may be more readily understood, currently preferred embodiments will now be further described by way of example with reference to the accompanying drawings, in which.

DETAILED DESCRIPTION

Figure 1:
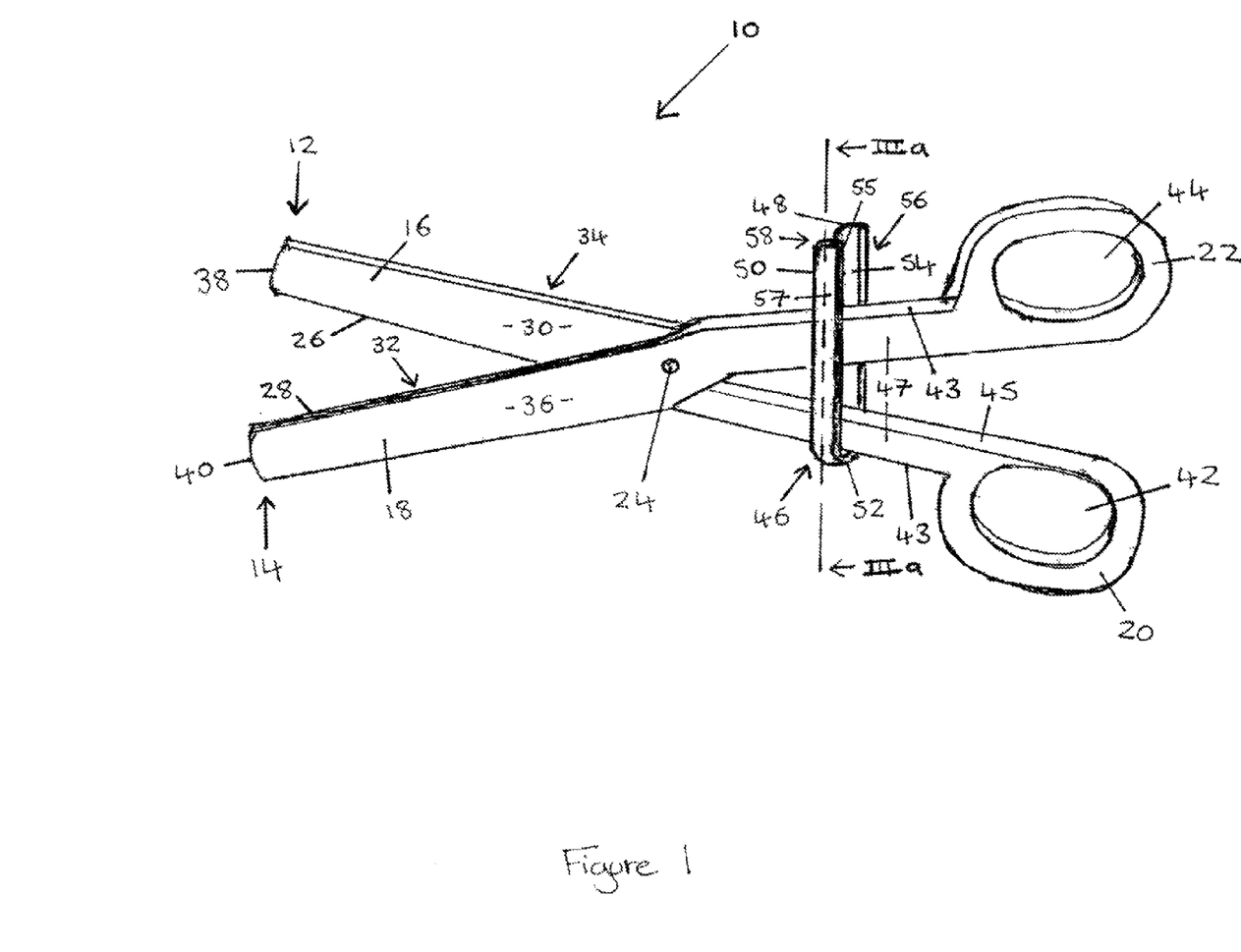
FIG. 1 is a perspective view of one embodiment of a pair of surgical scissors according to the invention.

Referring firstly to FIG. 1, there is shown a pair of surgical scissors 10 having first and second elongate scissor members 12, 14. In conventional manner, each scissor member 12, 14 has a distal blade portion 16, 18 and a proximal handle portion 20, 22 and the scissor members 12, 14 are pivotally connected to each other by a rivet, screw, stud or pin 24 at a pivot axis between the blade portion 16, 18 and the handle portion 20, 22. Also conventionally, the blade portion 16, 18 has a cutting edge 26, 28, a contacting face 30, 32, an outer face 34, 36 and a distal tip 38, 40, and the handle portion 20, 22 has outer faces 43 and a contacting face 45. A finger opening 42, 44 is provided at the proximal end of the handle portion 20, 22.

Unconventionally, in accordance with the invention, a restraining member 46, which may also be referred to as a channel member, is associated with the first handle portion 20 and may be integral with, or distinct from but attached to, the first handle portion 20. A restraining member 46 attached to the first handle portion by welding is shown in FIG. 1.

The restraining member 46 is substantially U-shaped and has two arms 48, 50 joined by a base 52. An open end 58 opposes the base 52. Each of the arms 48, 50 has an inner face 54, 55 and an outer face 56, 57. As shown in FIG. 1, the base 52 of the restraining member 46 is attached to the outer face 43 of the first handle portion 20 at a position approximately midway along the length of the first handle portion 20 and the arms 48, 50 extend in parallel away from the base 52 and the first handle portion 20, such that the restraining member 46 defines a channel or slot between the arms 48, 50 for receiving both the first and second handle portions 20, 22.

As per conventional scissors the cutting plane is perpendicular to the pivot axis and in accordance with the invention, as shown in FIG. 1, the arms 48, 50 of the restraining member 46 lie parallel to the cutting plane. The arms 48, 50 extend in a direction transverse to the length of the first handle portion 20 towards the second handle portion 22 and the inner faces 54, 55 of the arms 48, 50 oppose the side faces 47 of the handle portions 20, 22. The longitudinal thickness of the restraining member 46 is relatively small compared to the length of the handle portions 20, 22 such that only a small proportion of the length of the handle portions 20, 22 is sandwiched between the arms 48, 50 and is received within the channel defined by the restraining member 46. For example, the longitudinal thickness of the restraining member 46 may be between approximately 5% and 20% of the length of the handle portions 20, 22.

The arms 48, 50 are spaced from one another to define a channel of sufficient width to accommodate the handle portions 20, 22, such that the side faces 47 of the second handle portion 22 abut the inner faces 54, 55 of the arms 48, 50 in a sliding fit. Alternatively, a small clearance may exist between one or more of the side faces 47 of the handle portions 20, 22 and the inner faces 54, 55 of the arms 48, 50. For example, the handle portions 20, 22 may be housed in the channel such that the side faces 47 of both handle portions 20, 22 abut the inner faces 54, 55 of the arms 48, 50.

Alternatively, the handle portions 20, 22 may be housed in the channel such that none of the side faces 47 of the handle portions 20, 22 abut the inner faces 54, 55 of the arms 48, 50 and a clearance exists between both of the handle portions 20, 22 and the inner faces 54, 55 of the arms 48, 50. Or, the handle portions 20, 22 may be housed in the channel such that the side faces 47 on one side of the handle portions 20, 22 abut the inner face 54 or 55 of the arm 48 or 50 and the side faces 47 on the other side of the handle portions 20, 22 do not abut the inner face 54 or 55 of the arm 48 or 50, such that a clearance exists on only one side of the handle portions 20, 22. The clearance should be sufficiently small so as to prevent relative movement of the handle portions 20, 22 in the lateral direction beyond a predetermined limit.

In conventional manner, the cutting action involves squeezing together the handle portions 20, 22 which pivots the distal tips 38, 40 of the blade portions 16, 18 towards each other, from an open to a closed position. During this movement, the opposing cutting edges 26, 28 of the first and second blade portions 16, 18 slide relative to each other in a mutually intersecting manner. The point of intersection and hence the point of contact between the opposing cutting edges 26, 28 is initially near the pivot 24 and moves distally along the cutting edges 26, 28 as the distal tips 38, 40 of the blade portions 16, 18 swing closer together.

In use, the restraining member 46 remains in a fixed position on the first handle portion 20 due to the attachment of the base 52 of the restraining member 46 to the first handle portion 20. The second handle portion 22 is free to move within and along the length of the channel defined by the restraining member 46. In the closed position, the inner face 45 of the second handle portion 22 is in contact with the inner face 45 of the first handle portion 20 and both handle portions 20, 22 are positioned towards the base 52 of the restraining member 46. As the scissors 10 move from the closed position to the open position, the second handle portion 22 moves within and along the channel defined by the restraining member 46 away from the base 52 and towards the open end 58.

The restraining member 46 may be of a sufficient length from the base 52 to the open end 58 so that the scissors may be opened to the maximum open position without the second handle portion 22 extending out of the open end 58 of the restraining member 46. Alternatively, the length of the restraining member 46 from the base 52 to the open end 58 may be such that in the maximum open position of the scissors the second handle portion 22 does extend out of the open end 58 of the restraining member 46. The latter situation may be desirable, for example, to aid in the manufacture or cleaning of the scissors.

The parallel positioning of the arms 48, 50 means that the width of the channel defined by the restraining member 46 is constant along its length, such that the restraining effect is maintained throughout the cutting stroke for effective cutting.

By virtue of the invention, the restraining member 46 restrains lateral splaying movement of the first blade portion 16 away from the second blade portion 18 by retaining the handle portions 20, 22 approximately in their original lateral position in the cutting plane, such that lateral movement of the handle portions 20, 22 does not go beyond predetermined limits. Such lateral splaying movement would be transverse to the length of the blade portions 16, 18 and parallel to the pivot axis defined by the pivotable connection 24. Throughout the majority of, if not all of, the cutting action, depending on the length of the restraining member 46, the handle portions 20, 22 are received within the restraining member 46, thus preventing lateral movement of the handle portions 20, 22 and thereby also preventing the first blade portion 16 from splaying away from the second blade portion 18. Advantageously, this enables cutting of tough or slippery items which might otherwise cause the blade portions 16, 18 to splay away from each other. If the blade portions 16, 18 begin to splay away from each other during use, the restraining member 46 has the effect of forcing or biasing the blade portions 16, 18 towards each other again in a lateral direction, thus opposing lateral splaying movement of the blade portions 16, 18 during cutting.

Figure 2:
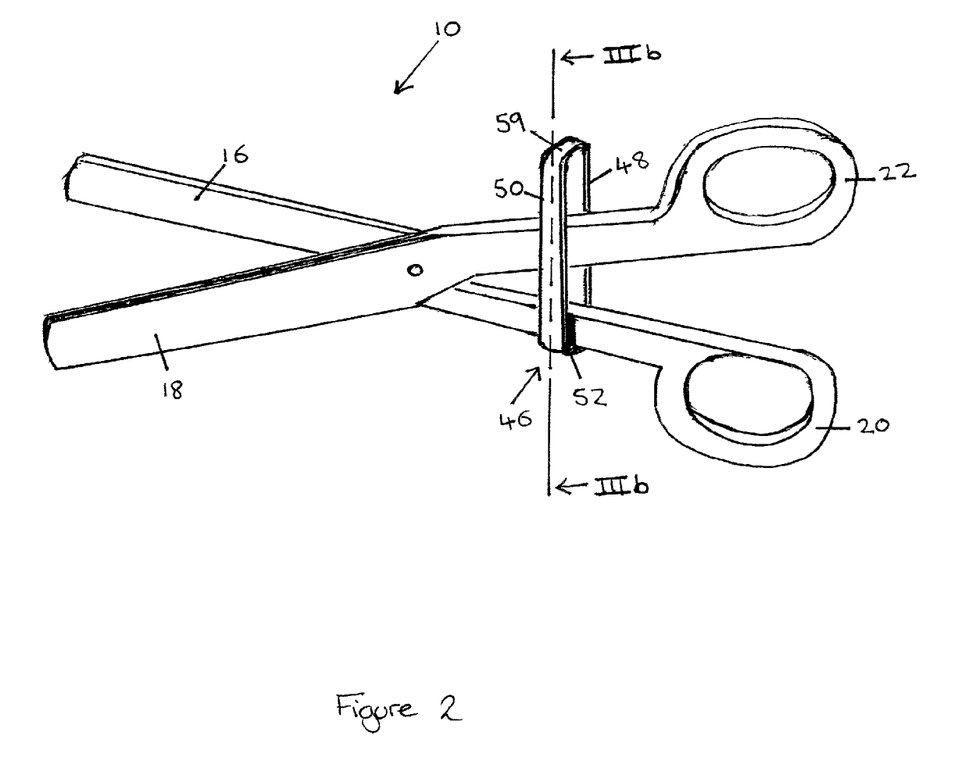
FIG. 2 is a perspective view of a second embodiment of a pair of surgical scissors according to the invention.

The embodiment of FIG. 2 differs from that of FIG. 1 in that the restraining member 46 is formed as a closed loop, which in this instance is substantially rectangular in transverse cross-section. The arms 48, 50 of the restraining member 46 are joined at one end by the base 52 and at the other end by a cross-bar 59, which opposes the base 52. This closed loop configuration avoids any divergence or lateral splaying of the arms 48, 50 of the restraining member 46, which may otherwise potentially occur over a prolonged period of repeated use. The restraining member 46 is of a sufficient length from the base 52 to the cross-bar 59 to allow the scissors to open to their maximum open position within the restraining member 46.

Figure 3:
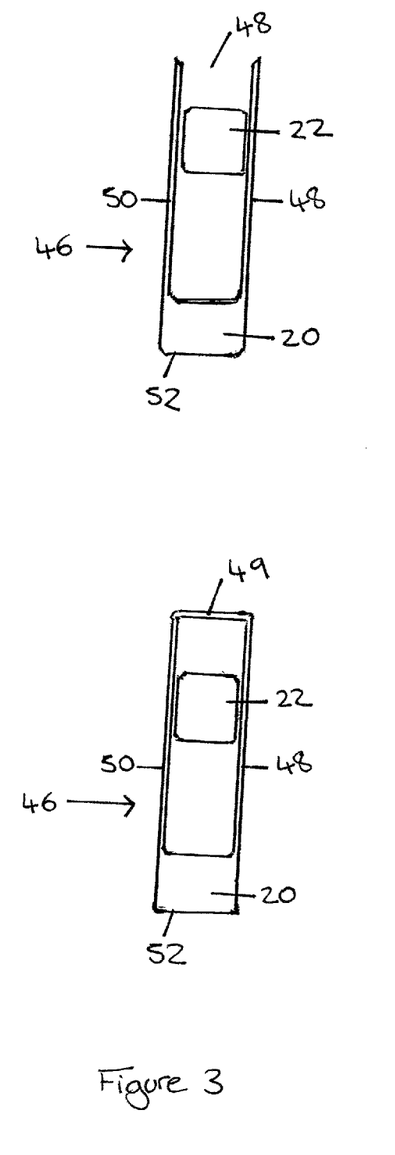
FIGS. 3(a) and 3(b) are cross-sections of the embodiments of FIGS. 1 and 2 taken along the lines IIIa and IIIb, respectively.

FIGS. 3(a) and 3(b) show cross-sectional views of the scissors of FIG. 1 and FIG. 2 taken along the lines IIIa and IIIb, respectively.

Figure 4:
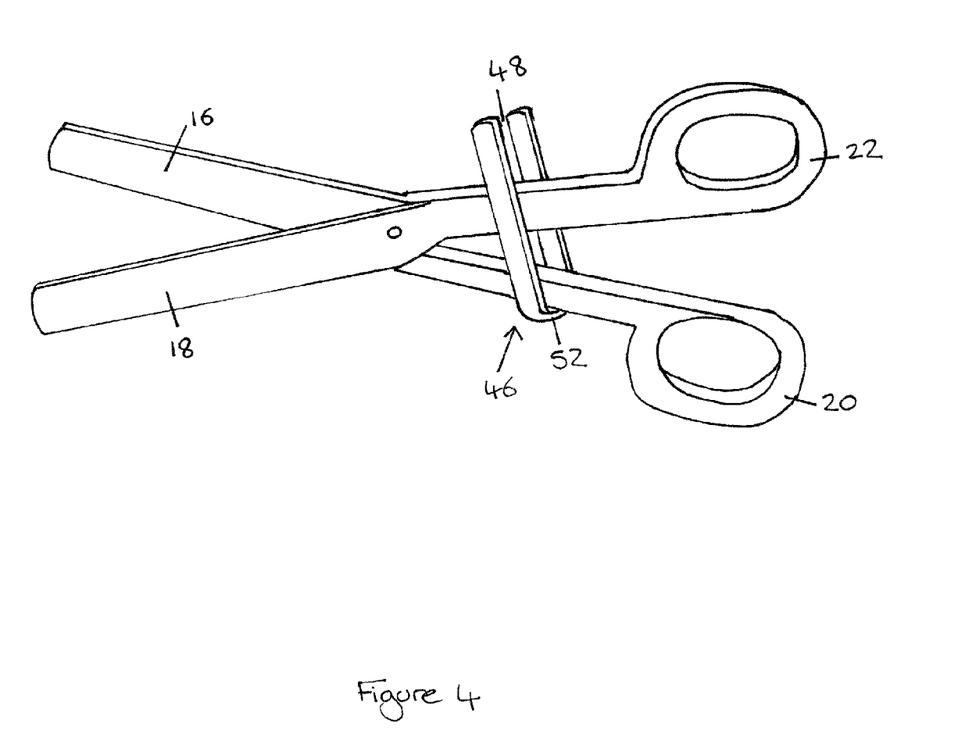
FIG. 4 is a perspective view of a third embodiment of a pair of surgical scissors according to the invention.
Figure 5:
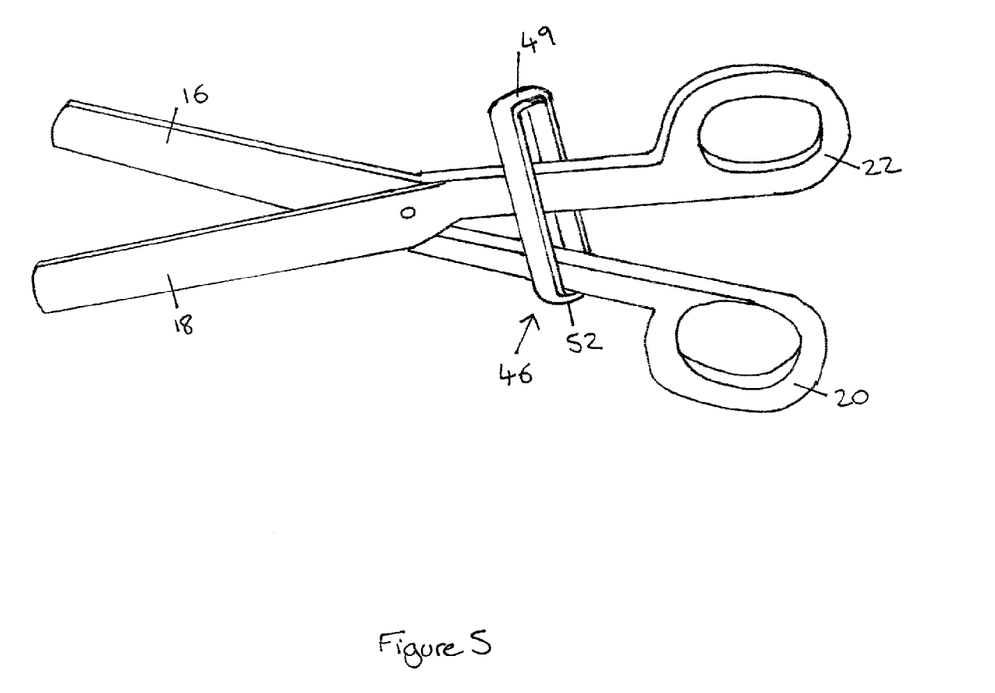
FIG. 5 is a perspective view of a fourth embodiment of a pair of surgical scissors according to the invention.

The embodiments of FIGS. 4 and 5 differ from those of FIGS. 1 and 2 in that the restraining member 46 is tilted away from the proximal end of the handle portions 20, 22 and towards the blade portions 16, 18 of the scissors 10. The base 52 of the restraining member 46 is attached to the first handle portion 20 as per the embodiments of FIGS. 1 and 2 but the open end 48 (as shown in FIG. 4) or the cross-bar 49 (as shown in FIG. 5) of the restraining member 46 is tilted in the cutting plane away from the proximal end of the handles portions 20, 22 and is angled towards the blade portions 16, 18. A restraining member tilted away from the proximal end of the handle portions and towards the blade portions is advantageous in that it avoids the user's thumb and/or fingers positioned in the thumb and/or finger openings of the handle portions from colliding and interfering with the restraining member.

The restraining member 46 may be tilted towards the blade portions 16, 18 at any angle that is suitable for avoiding potential interference with the thumb and/or fingers of the user. Typically, the restraining member 46 is tilted in the cutting plane towards the blade portions 16, 18 at an angle of between approximately 10 and 70 degrees relative to the pivot axis, preferably between 20 and 60 degrees, more preferably between 30 and 50 degrees and most preferably 45 degrees. The length of the restraining member 46 may be varied depending upon the angle of the tilt so that the restraining member 46 is of a sufficient length from the base 52 to the open end 58 or the cross-bar 59 to allow the scissors 10 to open to their maximum open position.

In an alternative arrangement, the restraining member 46 of any of the embodiments shown in FIGS. 1 to 5 may be integral with, or distinct from but attached to, the second handle portion 22 instead of the first handle portion 20.

In variants of any of the embodiments of the invention, the restraining member may be integrally formed with the first or second handle portions or may be formed separately from and attached/joined to the first or second handle portions. Any suitable means of attachment may be used, for example, welding, bonding, or one or more rivets, screws, studs, pins or other suitable fastener. Preferably, the restraining member is manufactured from metal, suitably the same metal as the scissors, and is integrally formed with the first or second handle portion of the scissors or most preferably is attached to the first or second handle portion of the scissors by welding. The restraining member may be attached to the outer face of the first or second handle portions and/or one or both of the side faces of the first or second handle portions.

In variants of any of the embodiments of the invention, it is possible for the restraining member to be formed without a base and for the arms to be integrally formed with or attached to the side faces of the first or second handle portions.

In variants of any of the embodiments of the invention, the arms of the restraining member may be straight, as shown in FIGS. 1 to 5, or alternatively they may be curved in the cutting plane such that the restraining member bends towards the blade portions. The arms may be curved along their entire length or alternatively they may be curved only along part of their length. Where they are curved only along part of their length, preferably a portion of the length of the arms closest to the open end or the cross-bar of the restraining member is curved towards the blade portions. Curvature of the restraining member in this manner is advantageous in that it helps to prevent the user's thumb and/or fingers positioned in the thumb and/or finger openings of the handle portions from colliding and interfering with the restraining member.

The restraining member may have any suitably sized and shaped transverse cross-section, for example it may have a substantially circular, square or rectangular transverse cross-section. The scissors may also comprise more than one restraining member.

The restraining member may be positioned at any point along the length of the first or second handle portions. It is preferable not to position the restraining member too close to the proximal end of the handle portions, otherwise there is an increased risk of the user's thumb and/or finger interfering with the restraining member. Also, it is preferable not to position the restraining member too close to the pivot axis between the blade portions and the handle portions as the effectiveness of the restraining member in restraining lateral splaying movement of the first blade portion away from the second blade portion may be slightly reduced. Typically, the restraining member is positioned anywhere between approximately one-third and two-thirds of the way along the length of the first or second handle portions, and preferably approximately mid-way along the length of the first or second handle portions.

One or both of the cutting edges of the blade portions may be adapted to improve the grip on tissue by the scissors before and during cutting. For example, one or both of the cutting edges may be serrated, or concave-curved to reduce the overall weight of the scissors and improve manageability, or may comprise a series of concave curvatures, or peaks and troughs, defining a wavy scalloped line. Alternatively, one or both of the cutting edges may be serrated and concave-curved, or serrated and comprising a series of concave curvatures. Serrated edges are advantageous in that they have an improved grip on the tissues and require sharpening less often than edges without serrations.

Although the scissors of the present invention have been described as surgical scissors, they may also be equally suitable for non-surgical and non-medical applications such as cutting textiles and other materials. The restraining member described herein may be applied to any size and shape of scissors.

Although particular embodiments of the invention have been disclosed herein in detail, this has been done by way of example and for the purposes of illustration only. The aforementioned embodiments are not intended to be limiting with respect to the scope of the appended claims. It is contemplated by the inventor that various substitutions, alterations, and modifications may be made to the invention without departing from the spirit and scope of the invention as defined by the claims.

The invention claimed is:

1. Scissors comprising:
a first and a second elongate member, the first elongate member and the second elongate member each having a handle portion and a blade portion;
a pivot connecting the handle portions and the blade portions for relative pivotal movement in a cutting plane during a cutting stroke;
a channel member with a base connecting two arms, the base is connected to the first elongate member on a side of the pivot opposite the blade portions; and,
wherein the handle portion of the first elongate member supports the channel member located a first distance away from the pivot, the channel member having a length that extends toward, embraces, and extends beyond the handle portion of the second elongate member to restrain movement of the handle portions out of the cutting plane and thus to resist relative lateral movement of the blade portions away from each other during the cutting stroke, the handle portion of the second elongate member being slidably moveable within and along the length of the channel member in the cutting plane.

2. The scissors of claim 1, wherein the arms extend parallel to one another.

3. The scissors of claim 1, wherein the channel member is U-shaped in transverse cross-section.

4. The scissors of claim 1, wherein the arms are joined together at both ends of the channel member such that the channel member is a closed loop.

5. The scissors of claim 4, wherein the channel member is substantially rectangular in transverse cross-section.

6. The scissors of claim 1, wherein the channel member is located approximately midway along a length of the handle portion of the first elongate member.

7. The scissors of claim 1, wherein the base is connected to the handle portion of the first elongate member by welding.

8. The scissors of claim 1, wherein the arms lie parallel to the cutting plane.

9. The scissors of claim 1, wherein the arms lie one each side of the cutting plane.

10. The scissors of claim 1, wherein each of the arms comprises an inner face.

11. The scissors of claim 1, wherein an inner side of at least one of the arms bears against the handle portion of the second elongate member.

12. The scissors of claim 1, wherein a longitudinal thickness of the channel member is between 5% and 20% of a length of the handle portions.

13. The scissors of claim 1, wherein the channel member extends in a direction substantially perpendicular to a length of the handle portion of the first elongate member.

14. The scissors of claim 1, wherein the channel member is inclined distally with respect to a length of the handle portion of the first elongate member.

15. The scissors of claim 1, wherein the channel member curves distally along its length from the handle portion of the first elongate member.

16. The scissors of claim 1, wherein the pivot allows a first maximum open position of the blade portions, and the channel member allows a second maximum open position of the blade portions, the first maximum open position being no less than the second maximum open position.

17. The scissors of claim 1, wherein the first distance is between one thirds and two thirds of a handle length of the handle portion of the first elongate member.

* * * * *